(12) United States Patent
Mendler (10) Patent No.: US 7,699,588 B2
(45) Date of Patent: Apr. 20, 2010

(54) CENTRIFUGAL PUMP

(75) Inventor: Nikolaus Mendler, Berg (DE)

(73) Assignee: Jostra AG, Hirrlingen (DE)

( * ) Notice: Subject to any disclaimer, the term of this patent is extended or adjusted under 35 U.S.C. 154(b) by 836 days.

(21) Appl. No.: 10/562,649

(22) PCT Filed: Jul. 2, 2004

(86) PCT No.: PCT/EP2004/007211

§ 371 (c)(1),
(2), (4) Date: Apr. 18, 2006

(87) PCT Pub. No.: WO2005/003565

PCT Pub. Date: Jan. 13, 2005

(65) Prior Publication Data

US 2006/0247486 A1     Nov. 2, 2006

(30) Foreign Application Priority Data

Jul. 4, 2003    (DE) ................................. 103 30 434

(51) Int. Cl.
     *F04B 35/04*      (2006.01)
(52) U.S. Cl. ................. 417/423.7; 417/423.1
(58) Field of Classification Search .............. 417/423.1, 417/423, 7
See application file for complete search history.

(56) References Cited

U.S. PATENT DOCUMENTS

| | | | |
|---|---|---|---|
| 5,158,440 A | 10/1992 | Cooper et al. |
| 5,324,177 A | 6/1994 | Golding et al. |
| 5,470,208 A | 11/1995 | Kletschka |
| 5,685,700 A | 11/1997 | Izraelev |
| 5,840,070 A | 11/1998 | Wamper |
| 5,947,703 A | 9/1999 | Nojiri et al. |
| 6,071,093 A | 6/2000 | Hart |

(Continued)

FOREIGN PATENT DOCUMENTS

EP      1 027 898      8/2000

(Continued)

*Primary Examiner*—Carl H Layno
*Assistant Examiner*—Yun Haeng Lee
(74) *Attorney, Agent, or Firm*—Michael J. Striker (57) ABSTRACT

The invention relates to a centrifugal pump, especially for blood, comprising a pump rotor which is arranged in a rotational manner and without a bearing in a liquid-tight and gas-tight closed housing, except for at least one inlet opening and at least one outlet opening. The rotor is also the rotor of a drive motor. The rotor is symmetrical with respect to the centre plane thereof and comprises an upper and a lower covering. The rotor and/or the pump housing are formed in such a way that the axial distances between the upper and the lower coverings and the upper and lower housing walls are smaller in the radially inner region of the rotor than in the radially outer region. In the radially inner region of the rotor, each lateral rotor chamber comprises a flow-restrictor gap which, when in operation, influences back flows oriented in a radially inward manner in the lateral rotor chambers, such that during an axial deflection of the rotor above and below the rotor, various pressure distributions appear, enabling forces acting upon the predominant surface of the coverings to be produced, the forces bringing about an axial stabilisation of the rotor and acting, in the same manner, against tilting of the rotor inside the housing.

7 Claims, 8 Drawing Sheets

U.S. PATENT DOCUMENTS

| | | |
|---|---|---|
| 6,227,797 B1 | 5/2001 | Watterson et al. |
| 6,227,817 B1 | 5/2001 | Paden |
| 2003/0124007 A1 | 7/2003 | Schima et al. |

FOREIGN PATENT DOCUMENTS

| | | |
|---|---|---|
| EP | 0 819 330 | 6/2001 |
| EP | 0 860 046 | 2/2003 |
| WO | 99/01663 | 1/1999 |
| WO | 00/32257 | 6/2000 |
| WO | 00/64508 | 11/2000 |
| WO | 01/42653 | 6/2001 |
| WO | 01/70300 | 9/2001 |
| WO | 01/72351 | 10/2001 |

CENTRIFUGAL PUMP

BACKGROUND OF THE INVENTION

The invention relates to a centrifugal pump, in particular for blood in cardiac substitution or assist devices, as generically defined by the preamble to claim 1. In particular, the invention relates to an electrically driven rotary pump of the radial/centrifugal type for permanent implantation in patients with terminal cardiac insufficiency who require mechanical support of their blood circulation.

Blood pumps, especially blood pumps or pumps for other vulnerable fluids, must meet special requirements:

1. High hydraulic efficiency, to keep the heat loss given up to the blood or fluid slight and to keep the energy storing means small.
2. Entirely contactless rotation of the rotor inside a hermetically sealed pump housing, thus precluding any wear, abrasion, and local heat development from mechanical friction.
3. Avoidance of standing eddies and flow stasis zones as well as minimal dwell times of the blood or fluid in the pump, to avoid damage to the fluid and the activation of blood coagulation.
4. In blood pumps, minimizing the cell-damaging shear stresses to which the blood is exposed on passing through the pump.
5. Security against mistakes by eliminating complex sensor-based positional regulations of the rotor while simultaneously reducing energy consumption.
6. Eliminating a drive motor with a supported shaft that is subject to wear.

Blood pumps of conventional design, in which the drive of the rotor is done by an electric motor with a supported shaft that penetrates the pump housing and is provided with a shaft seal are therefore unsuited for permanent implantation. Hermetically sealed housings, through whose wall the pump rotor is set into rotation by means of a magnetic coupling, do eliminate leaks but still require an external electric motor. Furthermore, the pump rotor in the housing must be guided by end journal bearings that are bathed with blood; these bearings wear and from local heating denature blood proteins and are capable of activating the coagulation system, which can lead to emboli from abrasion and clots.

A completely contact-free rotation of the pump rotor in the blood can be achieved by means of passive and active magnet bearings, hydrodynamic slide bearings, or a combination of these principles.

Any possible use of this principle must take Earnshaw's theorem into account, which states that it is not possible to keep a body floating in space in a stable position by means of constant magnetic, electrical, or gravitational fields. Any apparent position of equilibrium is in fact unstable, since the body is in that case at a maximum of potential energy. In at least one axis in space, a stabilizing force acting on the system is therefore required. This force must be all the greater, the farther the body is located from the site of the maximum energy. Conversely, only slight restoring forces are necessary, if the system is located a priori in the vicinity of the unstable equilibrium.

Magnetically supported pump rotors with open blades are described in U.S. Pat. No. 6,227,817. Here, a combination of passive magnet bearings for radial stabilization and sensor-based active axial electromagnetic suspension is described. Besides the complex production, this embodiment requires an elongated gap between the rotor and the housing with only inadequate purging and high energy consumption for the axial stabilization, which must counteract the considerable hydraulic axial shear that is generated by an open impeller.

Blood pumps with complete magnetic suspension are described in European Patent Disclosures EP 0 819 330 B1 and EP 0 860 046 B1. Here, the rotor of the pump is embodied as a rotor of a permanent-magnetically excited electrical synchronous machine. The torque is generated by a revolving, radially engaging electromagnetic stator field, as is the position control of the rotor in the radial direction. Separate control windings of the stator are used for this purpose, which convert the signals of spacing sensors into centering forces by way of electronic closed-loop control circuits. Because of the externally located stators for the drive and positional regulation, this pump requires a relatively large amount of installation space. The stabilization of the other three spatial degrees of freedom that cannot be actively triggered is done by passively acting magnetic reluctance forces. Problems also arise in versions with open impellers because of the high hydrodynamic axial shear, which unavoidably occurs. To overcome them, additional active or passive magnet bearings as well as hydrodynamic aids in the form of nozzles, impact plates, inflow tubes, flow resistors, and sealing gaps are proposed, all of which increase the complexity of the system, lessen its efficiency, create flow stasis zones, induce high shear stresses, and are thus entirely unsuitable for the realization of a blood pump, especially for permanent implantation.

Bearingless blood pumps with magnetic suspension and open impellers are also disclosed in U.S. Pat. No. 6,071,093. However, the transmission of the torque is done here by an axially engaging encircling electromagnetic stator field. The axial rotor position and the tilting of the rotor in the housing are stabilized by a sensor-based electromagnetic feedback by means of actuators, while at the same time passive permanent magnet bearings provide the radial centering. The problems of the axial instability of an open impeller are solved—besides by electromagnetic feedback by means of sensors and actuators—by a fluidically effected compensation. This compensation is based on the action of a throttle gap, located on the outer circumference of the rotor, which as a function of the axial rotor position either limits or enables the back flow on the side of the rotor facing away from the blades. In this version as well, there is the risk of high shear stresses and the generation of flow stasis zones on the back side of the rotor.

U.S. Pat. No. 5,947,703 also describes an electromagnetically suspended centrifugal pump. Here, the drive of a covered impeller is effected by means of a unilaterally axially engaging permanent-magnet face-end rotary coupling or by an encircling stator field, whose forces of attraction cause the pump rotor at the housing to strike the wall unless the axial rotor position is regulated by a sensor-based active electromagnetic feedback. If this regulation fails, mechanical emergency bearings in the form of end journal bearings, slide bearings, point bearings, and hydrodynamic pressure bearings are provided, which are meant to prevent a life-threatening seizing of the pump rotor. All these proposals share the disadvantage of mechanical wall contact between the rotor and the housing, with the known consequences of damage to the blood.

International Patent Disclosure WO 01/42653 A1 describes a centrifugal pump with electromagnetic active position regulation of the pump rotor in all six degrees of freedom in space; the position, speed and acceleration of the rotor are not detected by sensors but derived from current signals of the active magnet bearings. This disadvantageously makes for an extremely complex mechanical construction of the rotor and multiple stators as well as extremely complex regulating electronics with an additional energy requirement, especially since to avoid high axial destabilizing forces, an ironless motor has to be used, which because of its poor efficiency heats up sharply.

The aforementioned disadvantages of active electromagnet bearing of the pump rotor were the impetus for a number of inventions in which complicated sensors and electronics were meant to be eliminated by means of hydrodynamic stabilization of the rotor/impeller.

For instance, in U.S. Pat. No. 5,324,177 and International Patent Disclosure WO 01/72351 A2, a hydrodynamic support bearing are used for radial stabilization of the rotor of an electrical direct current machine, and it carries the open pump rotor. A disadvantage here is the long axial length of the narrow, eccentric bearing gap, in which high shear stresses are operative, and which for being washed out requires auxiliary blades and a purging circuit from the high- to the low-pressure side of the pump. This arrangement involves the familiar risks of high shear and inadequate heat dissipation, which lead to traumatization of the blood.

These disadvantages are partly avoided in U.S. Pat. No. 6,227,797. In it, in a rotationally symmetrical housing, the pump rotor is embodied such that its surfaces on all sides form wedge-shaped gaps relative to the housing, in the direction of the active faces inclined in the direction of the relative motion. The pump rotor and housing thus form a hydrodynamic three-dimensional slide bearing, as is entirely usual in mechanical engineering. The supporting fluid film of blood, which acts as a lubricant for these wedge-shaped faces, covers a large area and especially at the circumference of the rotor is subjected to high shear stress, for which typical values of 220 $N/m^2$ are given. This shear stress is thus within a range in which damage to blood cells, especially thrombocytes, from shear must be feared. Other disadvantages of this version are that the open pump rotor is surrounded on all sides relative to the housing by narrow gaps, in which high viscous friction prevails. The necessity of splitting the rotor into segmental blocks, to allow the blood to pass from the inlet to the outlet of the pump, stands in the way of optimizing the fluid-mechanical efficiency of the pump. Accordingly, for an implantable blood pump with low energy consumption, which is a worthwhile goal, the stated hydraulic degrees of efficiency of at most 11% are prohibitively low. The long axial length of the rotor moreover causes hydrodynamic radial shear on the rotor, which can necessitate a split spiral conduit, which favors the development of thromboses. Moreover, the housing is complicated to manufacture. The embodiment of a covered pump rotor shown in FIG. 20, with a surface structured in wedgelike shape in sectors, does not overcome these disadvantages, especially since it cannot be seen what path the blood is supposed to take to flow through such a rotor.

A quite similar version of hydrodynamic axial stabilization of an open pump rotor by means of floating wedge-shaped faces inclined in the direction of rotation is described in International Patent Disclosure WO 00/32256. Once again, the disadvantages are damage to the blood and a complicated housing construction. The radial centering of the rotor is moreover done here not by hydrodynamic but rather by permanent magnet reluctance forces of a face-end rotary coupling or of an electromagnetic drive motor.

WO 99/01663 discloses a hydraulically suspended pump rotor, which is meant to float by Archimedes buoyancy, since it has the same density as the fluid to be pumped. This pump must be embodied with two inlets, or the inflow must be diverted inside the pump by 180°; the result is large wetted internal surfaces as well as questionable hydrodynamic stability.

WO 01/70300, for hydrodynamic stabilization, proposes a conical rotor with slitlike openings for the flow to pass through and guide faces, through which a fluid flow oriented counter to the housing is generated that is meant to have a stabilizing effect. If that does not suffice, an active magnet bearing is provided for radial stabilization, but this represents additional electronic complication and expense. In a number of patents (WO 00/32257, WO 00/64508, EP 1 027 898 A1, and U.S. Pat. No. 5,840,070), combinations of the most various principles are employed for stabilizing the pump rotor: ball-spur bearings, passive permanent magnet radial bearings, active-sensor-based electromagnetic axial bearings, hydrodynamic wedge-shaped face bearings with both an axial and a radial action, supplemented by such auxiliary constructs as profiling of the rotor and/or of the housing by means of overlays, ribs, and disks, conduits, and other provisions.

It is notable that at least three of these principles must always be employed in combination in order to assure contactless rotation of the impeller in the pump, and that in the wedge-shaped face bearings, given the stated gap width of approximately 0.013 to 0.038 mm, shear stresses (of over 600 $N/m^2$) occur, which are highly likely to damage blood.

A critical assessment of the prior art discussed consequently shows that the contactless rotation of the rotor of a centrifugal pump in the housing is attained either by means of high complexity and expense for sensors and electromagnetic regulation, or at the cost of a high hydrodynamic load on the blood from damaging shear stresses.

BRIEF SUMMARY OF THE INVENTION

The object of the present invention is to create a centrifugal pump with a bearingless rotor, in which in a simple way that protects fluid, the rotor can be stabilized in the axial and radial directions and has high efficiency.

This object is attained with a centrifugal pump having the characteristics of claim 1. The dependent claims recite advantageous refinements.

The axial stabilization of the pump rotor is done hydrodynamically by means of the fluid pumped through the rotor. To that end, the radially inward-oriented fluid flow between the rotor surfaces and the housing, which occurs because of the prevailing pressure difference between the radially outer and the radially inner regions of the pump housing, can generate the hydrodynamic forces for axial stabilization of the rotor. The rotor is embodied symmetrically to its center plane and has an upper and a lower covering. As a result, defined flow conditions result for the lost fluid flow oriented inward from the periphery, which flow can be used to axially stabilize the rotor.

According to the invention, the flow-dictated pressure drop in the side chamber of the axially symmetrical pump rotor, covered on both ends, is accordingly utilized: The outlet pressure generated by the pump at the rotor circumference is reduced to the inlet pressure toward the center by way of the back flow through the rotor side chambers. Because the rotor and/or the pump housing are shaped such that the axial spacings between the upper and lower coverings of the rotor and the upper and lower housing walls are less in the radially inner region than in the radially outer region of the rotor, a throttling action arises in the central region of the coverings when the fluid flows from the outside inward. The throttle gap causes the great majority of the pressure loss, and as a result a higher pressure continues to be preserved in the peripheral region of the coverings, and hence a force component is exerted on the entire covering that acts counter to narrowing the gap. This force is greater, the narrower the gap in the central region of the covering.

Thus if the rotor moves upward, the upper gap narrows. The resultant increase in the pressure of the fluid then presses the rotor downward again. Conversely, the fluid presses the rotor upward again if the rotor should move downward from the middle. Hence a hydrodynamic stabilization of the axial position of the pump rotor occurs automatically. Upon axial deflection of the rotor, the throttle gap is narrowed in the direction of the deflection and widened on the opposite side. On the side of whichever gap is wider, this causes a relative increase in the radially inward-oriented back flow and hence an asymmetrical hydrodynamic pressure drop. The rotor side chambers form parallel-connected nozzles, whose differential pressure is operative on the entire surface of both closed coverings of the rotor, and an axially stabilizing restoring force acting symmetrically to the position of repose of the rotor is thus generated. The rotor is therefore stabilized against deflection in the z axis.

The same is true for the tilting of the rotor, or in other words a rotary motion about the x and y axes. In that case as well, the axially symmetrical throttle gaps are narrowed and widened contrary to one another, with the consequence of a restoring force in the direction of a stable rotor position in the housing. Until now, these effects have not been utilized in bearingless pumps. An essential precondition for the desirable minimizing of the stabilizing energy required is the axial symmetry, according to the invention, of the pump rotor and the rotor side chambers.

The spacings between the upper and lower rotor coverings and the upper and lower sides of the housing can decrease continuously, for instance. Preferably, however, annular constrictions can also be embodied in the radially inner region of the rotor and housing, between the rotor coverings and the upper and lower housing walls, and these constrictions bring about the increased pressure drop in the fluid and the desired increase in pressure. The farther inward the constriction is located, the more engagement area is available for the fluid to stabilize the axial position of the pump rotor.

The radial stabilization of the rotor can be done purely passively on the basis of reluctance forces. The hydrodynamic radial shear, which urges the rotor out of the center of the rotary motion, should be minimized. To that end, the projection area of the rotor in the x-y/z plane is preferably kept minimal as an active face of radially destabilizing pressure forces. It is determined solely by the thickness of the coverings of the rotor. The rotor may preferably be made entirely of paramagnetic and/or ferromagnetic material and permanently magnetized. In that case, no encapsulation of discrete permanent magnets is necessary, which contributes to increasing the radial projection area. A further provision against radial instability is to provide a circular, rotationally symmetrical annular gap, which divides the rotor side chambers from a spiral conduit that carries the pumped flow tangentially away. As a result, a constant flow resistance to the fluid that emerges from the rotor is generated, and hence a radial pressure force on the rotor that acts uniformly via the circumference of the rotor is generated. The third provision against radial instability comprises a suitable design of the spiral conduit that carries the flow away, in which radially destabilizing pressure forces in the region of the tongue are avoided.

The drive of the pump is preferably done in the form of a permanently excited electrical synchronous machine, whose rotor is formed by the rotor of the pump, which is located between two symmetrical stators with a wide air gap. The stators may be rotated counter to one another, as can the permanent magnet regions of the rotor that are split into two planes. The pole coverings and the topology of the electromagnetic flux linkage can be optimized so that with the least mass of magnetic material, high efficiency and low waviness is attained, that is, high constancy of the torque and low axial rigidity of the magnet system, thereby making the hydrodynamic suspension of the rotor possible. Simultaneously, the magnetic reluctance forces between the stators and the rotor are utilized for centering the rotor radially.

The centrifugal pump of the invention is especially suitable for use as a blood pump and in that form for implantation in the human body, since it requires only little space and is absolutely maintenance-free. The pump can be used as a blood pump for assisting the cardiac activity of a patient or in conjunction with a heart-lung machine. The pump can also be used to pump other fluids, particularly aggressive and dangerous fluids or vulnerable fluids, in which contact with the outside is to be avoided. The components of the pump that come into contact with the fluid can be provided with a coating adapted to the particular fluid.

BRIEF DESCRIPTION OF THE SEVERAL VIEWS OF THE DRAWINGS

Preferred exemplary embodiments of the centrifugal pumps of the invention are described below, particularly for use as permanently implantable blood pumps for cardiac assistance, in further detail and in terms of their function in conjunction with drawings.

Shown are:

FIG. 4, graphs showing the radial course of the pressures in the rotor side chambers;

a) for an axially middle position of the rotor in the housing;

b) with axial offset of the rotor toward the inlet of the housing;

DETAILED DESCRIPTION OF THE INVENTION

Figure 1:
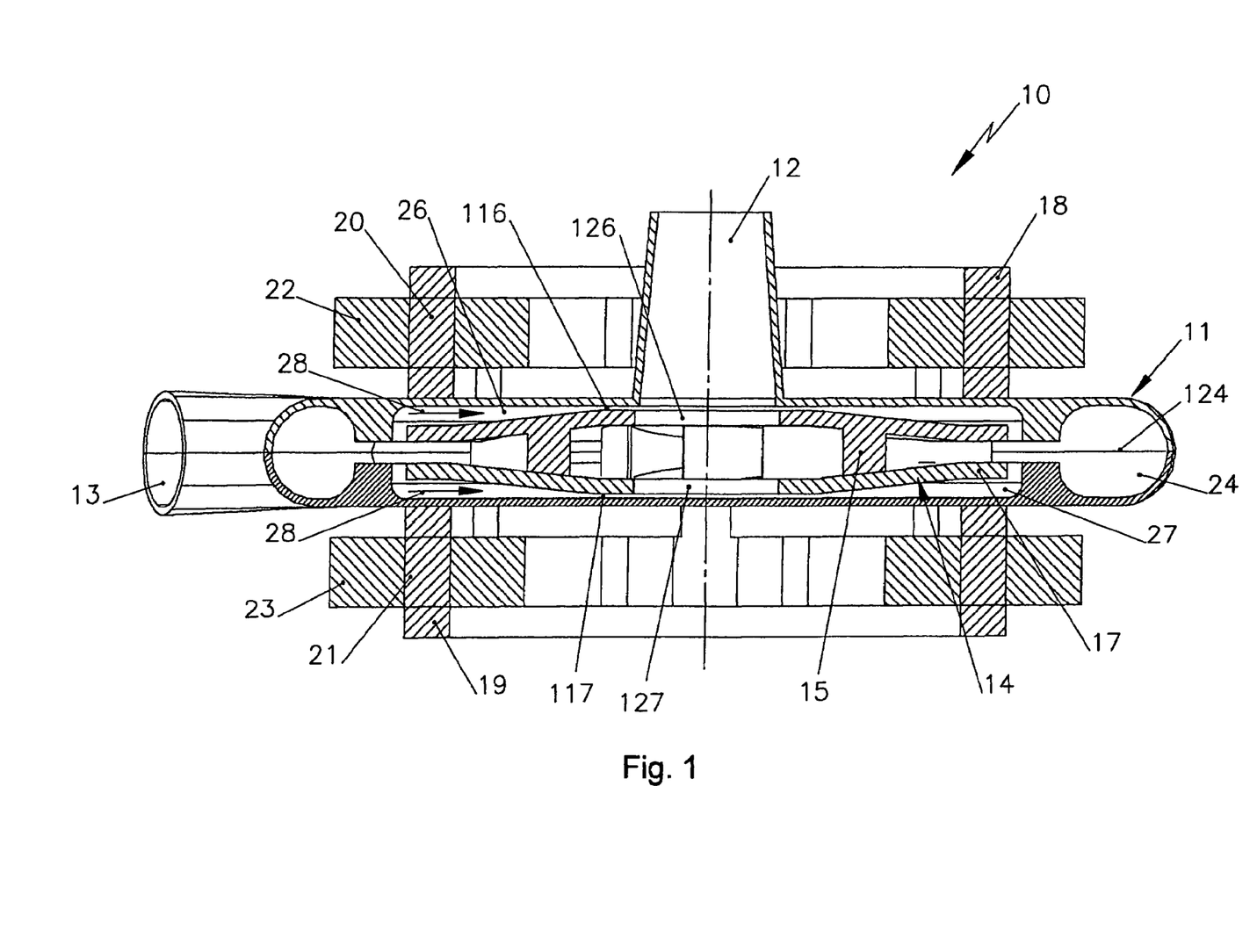
FIG. 1, a cross section through an exemplary embodiment of a centrifugal pump of the invention.

The centrifugal pump 10 of FIG. 1 has a pump housing 11 with an inlet 12 and a tangential outlet 13 for blood or some other fluid. Otherwise, the pump housing 11 is closed in a fluid- and gas-tight manner. A pump rotor 14 is located in bearingless and rotatable fashion in the interior of the pump housing 11. With the aid of the pump rotor 14, the blood flowing in through the opening 12 is pumped radially outward and toward the outlet 13. To that, the pump rotor has feeder blades 15. The feeder blades 15 are covered at the top and bottom by an upper covering 16 and a lower covering 17.

The pump rotor 14, at least in its circumferential region, has permanently magnetized regions. In the example shown, however, it is made entirely of a paramagnetic and/or ferromagnetic material. Thus at the same time it forms the rotor for a drive motor, which besides the rotor 14 has two annular stators 18, 19, which have many uniformly distributed portions 20, 21, protruding in the direction of the rotor 14, that are each surrounded in a preferred embodiment by a respective winding 22, 23. However, winding arrangements are also conceivable in which a plurality of the axially protruding portions 20, 21 are enclosed=["surrounded"] by a winding 22, 23. The two stators 18, 19 are located outside the housing, so that the drive of the pump rotor 14 is effected in contactless fashion. As a result, only minimal loads occur for the blood to be pumped in the housing 11. The rotor 14 and the housing 11 are preferably coated, where they come into contact with blood, with a blood-compatible material.

The stators 18, 19 generate a rotating magnetic flux in the space between the regions 20, 21 and the rotor 14. Simultaneously, the two stators assure radial centering of the rotor 14 in the housing 11. The radial centering is effected purely passively, based on reluctance forces.

Below, the way in which in the pump 10 the stabilization of the pump rotor 14 against displacement in the housing 11 in the axial direction is accomplished by hydrodynamically generated pressure forces will be described.

Figure 2A:
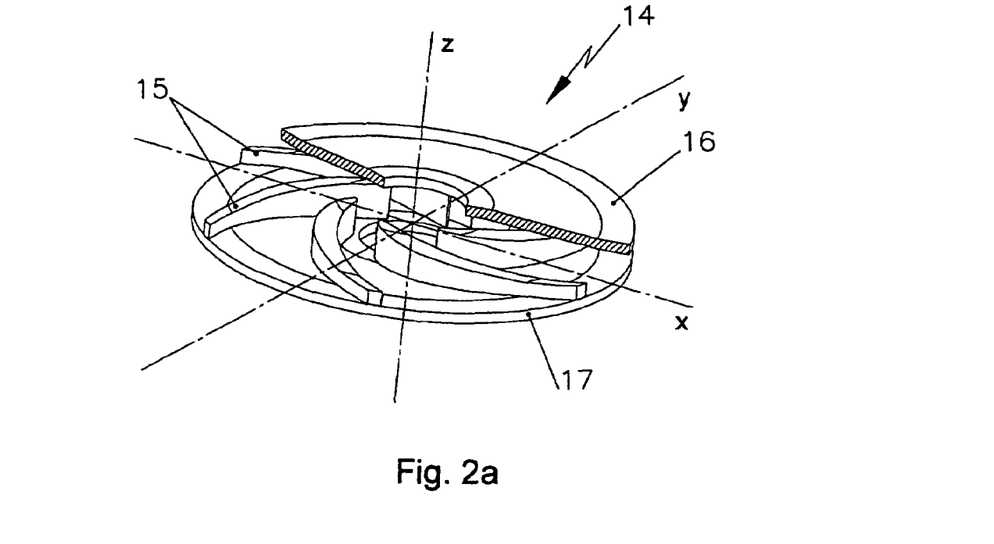
FIG. 2a, a perspective view of the rotor of the pump of FIG. 1 with the upper covering partly removed.

The rotor 14 has coverings 16, 17, which are entirely axially symmetrical and smooth and which enclose blades 15, whose number and shape can be optimized to suit flow-dynamic requirements (FIG. 2a). In the embodiments shown here, the number of blades is six. The blood enters on the intake side through an opening 126 into the rotor 14. A second opening 127 of the same size in the lower covering serves to equalize pressure between the rotor side chambers 26, 27, so that regardless of the pressure and flow conditions prevailing there, the same pressure always prevails at the edges, oriented toward the center, of the openings 126, 127 (FIG. 1). The blood leaves the rotor 14 after passing through the blade conduits at the outer circumference into the annular gap 124 leading away and finally into the spiral conduit 24 at high pressure.

Figure 2B:
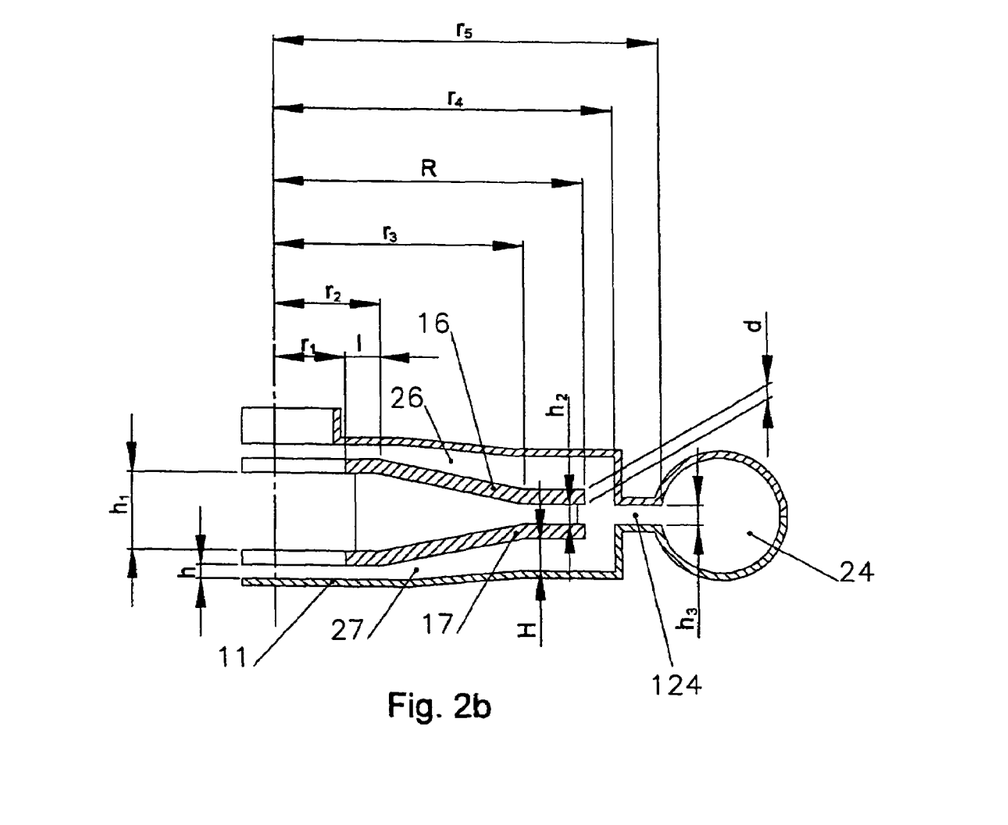
FIG. 2b, a schematic cross section through the rotor and housing of the pump of FIG. 1 for illustrating the geometric parameters.

The rotor side chambers 26, 27 in FIG. 2b are defined by the coverings 16, 17 of the rotor 14 and the walls of the housing 11. In a centrifugal pump with a covered pump rotor 14, two flow directions prevail in these rotor side chambers 26, 27: The boundary layer, adhering directly to the rotating coverings 16, 17, is moved outward by centrifugal force, while the built-up pressure near the stationary housing 11 and in the predominant volume of the side chamber 26, 27 generates a radially inward-oriented back flow 28, which is known as a short-circuit flow or leakage flow and which lessens the hydraulic efficiency. In industrial pump construction, labyrinth seals near the axis, among other provisions, serve to reduce these losses. For blood pumps, their use is recommended because of the development of high shear stresses and flow stasis zones that are difficult to purge thoroughly.

The symbols used hereinafter to describe the geometry of the pump rotor and the housing are shown in FIG. 2b. They stand for the following:

R Radius of the covering of the rotor;
$r_1$ Radius of the inflow openings into the rotor;
$r_2$ Radius at the inlet into the throttle gap;
$r_3$ Radius at the beginning of the permanent magnet regions of the coverings;
$r_4$ Inner radius of the housing;
$r_5$ Outer radius of the circular annular gap;
H Width of the rotor side chamber at the rotor circumference;
h Axial width of the throttle gap;
$h_1$ Blade height at the rotor inlet;
$h_2$ Blade height at the rotor circumference;
$h_3$ Height of the circular annular gap;
l Radial length of the throttle gap $(r_2-r_1)$;
d Thickness of the coverings.

In the pumps according to the invention, the unavoidable energy loss of the radial back flow 28 in the rotor side chamber 26, 27 is utilized for generating a hydrodynamic restoring force against axial migration of the rotor by means of a novel geometric design of this gap space 26, 27, as is shown in FIG. 3.

Figure 3A:
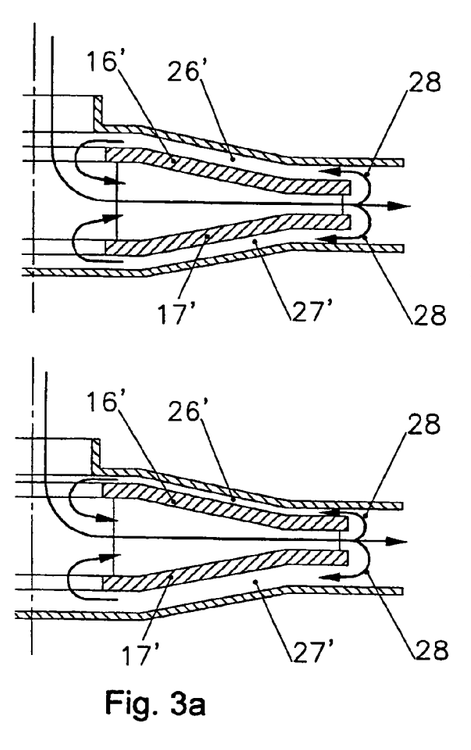
FIG. 3a, 3b, a schematic illustration of the flow conditions through the rotor of a centrifugal pump with a constant width and a radially inwardly decreasing width, respectively, of the rotor side chamber.

In FIG. 3a, a rotor side chamber is shown, with a constant axial width over the radius of the covering 16', 17'. In the middle position of the rotor, equal flow intensities occur in both rotor side chambers, since the pressures are equal at the circumference and in the center of the rotor, and thus symmetrical pressure distributions act on the coverings. If the rotor in FIG. 3 deflects axially toward one side, the flow is speeded up in the narrower rotor side chamber, and consequently the pressure on the covering drops there, and the opposite occurs in the widened, diametrically opposite rotor side chamber with a delayed flow there, in obedience to Bernoulli's Law and in analogy with the familiar "hydrodynamic paradox". The compensating motion is therefore reinforced until the rotor strikes the wall of the housing.

The geometric design according to the invention of the rotor side chambers 26, 27 turns this effect around (FIG. 3b): The gaps between the coverings 16, 17 and the housing 11, in their radially inner regions, each have—relative to the rest of the gap—a major axial narrowing over a short radial length, so that directly before the inlet opening of the rotor, there is one symmetrical throttle gap 116, 117 (FIG. 1) is embodied on each side. The leakage flow 28 here meets a high terminal serial resistance. In a middle position of the rotor, pressure equilibrium prevails in the upper and lower rotor side chambers. Upon axial deflection of the rotor, the proportion of the throttle gap in the gap that is becoming narrower compared to the total gap resistance becomes greater and greater. As a result, the pumping pressure at the rotor circumference in the narrowed rotor side chamber is approximately preserved radially inward to close to the throttle gap and only there is it sharply reduced via the terminal resistance of the throttle. In the diametrically opposed gap of increasing size, the influence of the throttle restriction becomes less and less. The pressure is reduced radially inward uniformly, beginning at the circumference, over the entirely length of the gap.

Figure 3B:
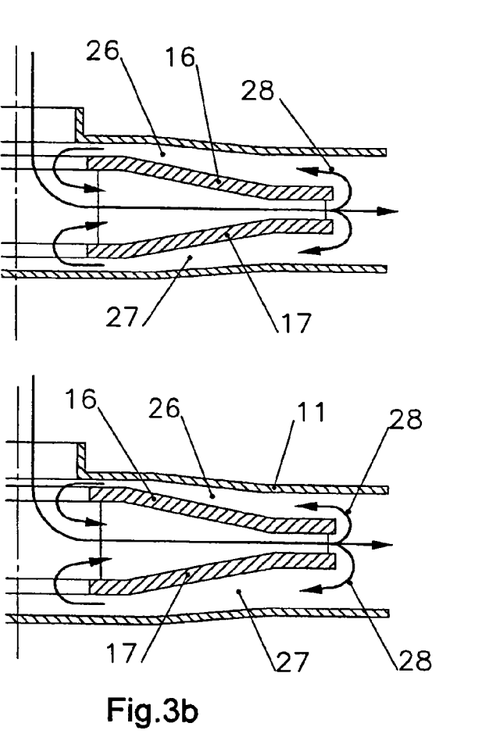

The resultant difference in the pressure forces on the closed coverings therefore generates a force, upon each axial deflection of the rotor from the middle position, that is proportional to the deviation and restores the rotor. It is understood that in the narrow, annular throttle gap 116 itself, which is axially plane-parallel to the housing, the aforementioned flow law still applies, and accordingly the accelerated flow in the narrower gap would destabilize the rotor in the direction of the narrowing. The effective area of the pressure forces, however, is only a small fraction here of the surface of the coverings, and hence the axially restoring forces greatly predominate.

Figures 4A, 4B:
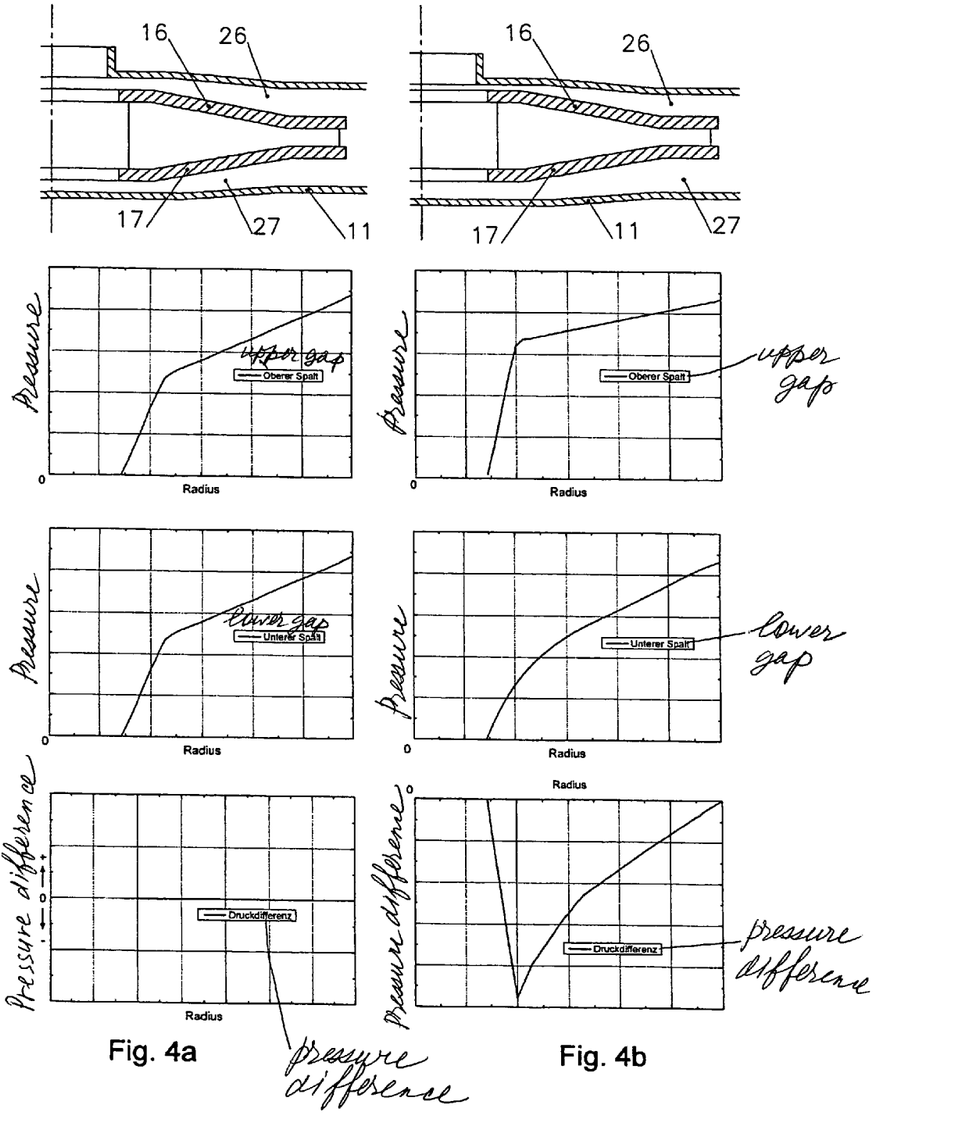

Measurements of a rotor (R=20 mm) in a pump of FIG. 1, for an axial offset of the rotor, have shown radial pressure courses in the rotor side chambers as shown in FIGS. 4a and b. Each axial offset (FIG. 4b) causes an asymmetry of the radial course of the pressure decrease in the rotor side chamber. The resultant pressure difference becomes operative, over the greatly predominant area of the coverings, as a restoring force that positions the rotor axially centrally.

Figure 5:
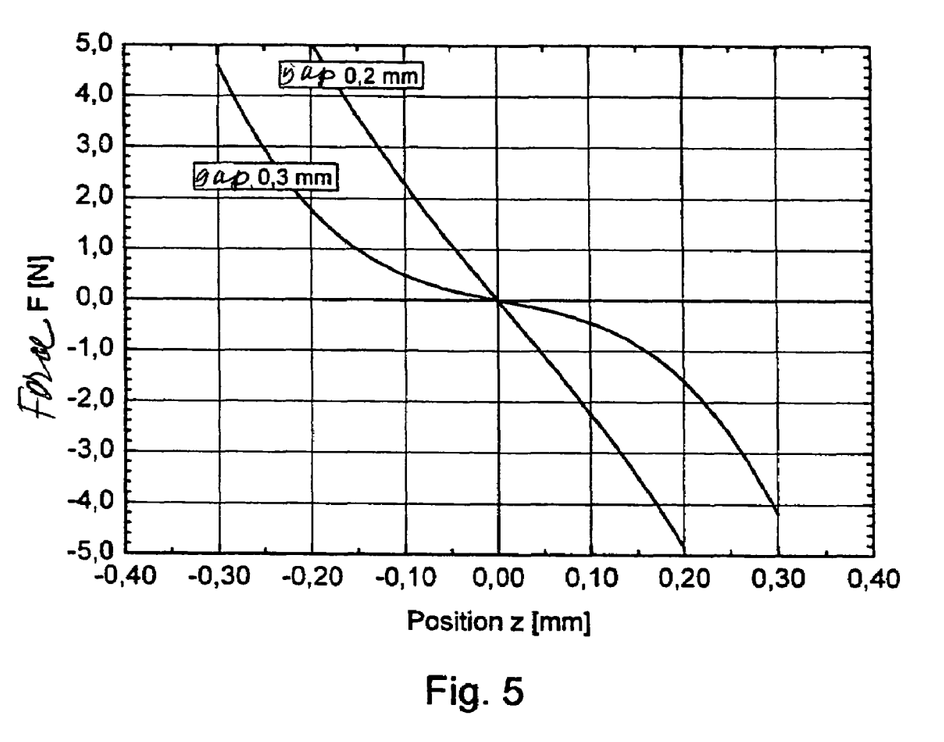
FIG. 5, a graph showing the course of the restoring force as a function of the axial deflection from the middle rotor position for throttle gaps of different widths.

The amounts of the restoring forces that result from the pressure differences of FIG. 4 are shown in FIG. 5. What is wanted is as great a rigidity dF/dz as possible over the entire range of the deflection in the direction z (FIG. 2a). It can be seen that a narrow throttle gap (h=0.2 mm) meets this requirement in linear fashion and more steeply than a wider gap (h=0.3 mm); in both cases, at maximal deflection, restoring forces of approximately ±5 N are attained, and this is done largely independently of the working pressure and pumping rate of the pump (120±20 mmHg, 5±2 l/min). For the geometry of the throttle gap, a ratio h/R in the range of from 0.016 to 0.008 and of l/R in the range of from 0.16 to 0.08 has proved especially favorable, as have corresponding heights of the throttle gap of from 0.32 mm to 0.16 mm and an axial length of from 1.6 to 3.2 mm, in the preferred embodiment having a radius R of the rotor of 20 mm. In the range of h/R<0.006, with increasing shear forces, the rigidity does not increase further. In the range of h/R>0.2, adequate restoring forces are not attained.

A rotational deflection of the rotor (FIG. 6) about the axes (x, y), or in other words tilting in the housing, causes a contrary narrowing and widening of the throttle gaps symmetrically to the axis of rotation and hence different radial courses of the leakage flows and the pressure decrease in the diametrically opposed rotor side chambers. The resultant differential pressure becomes operative as a restoring pressure force on the entire area of both coverings and rotates the rotor back into its neutral position.

Figure 6:
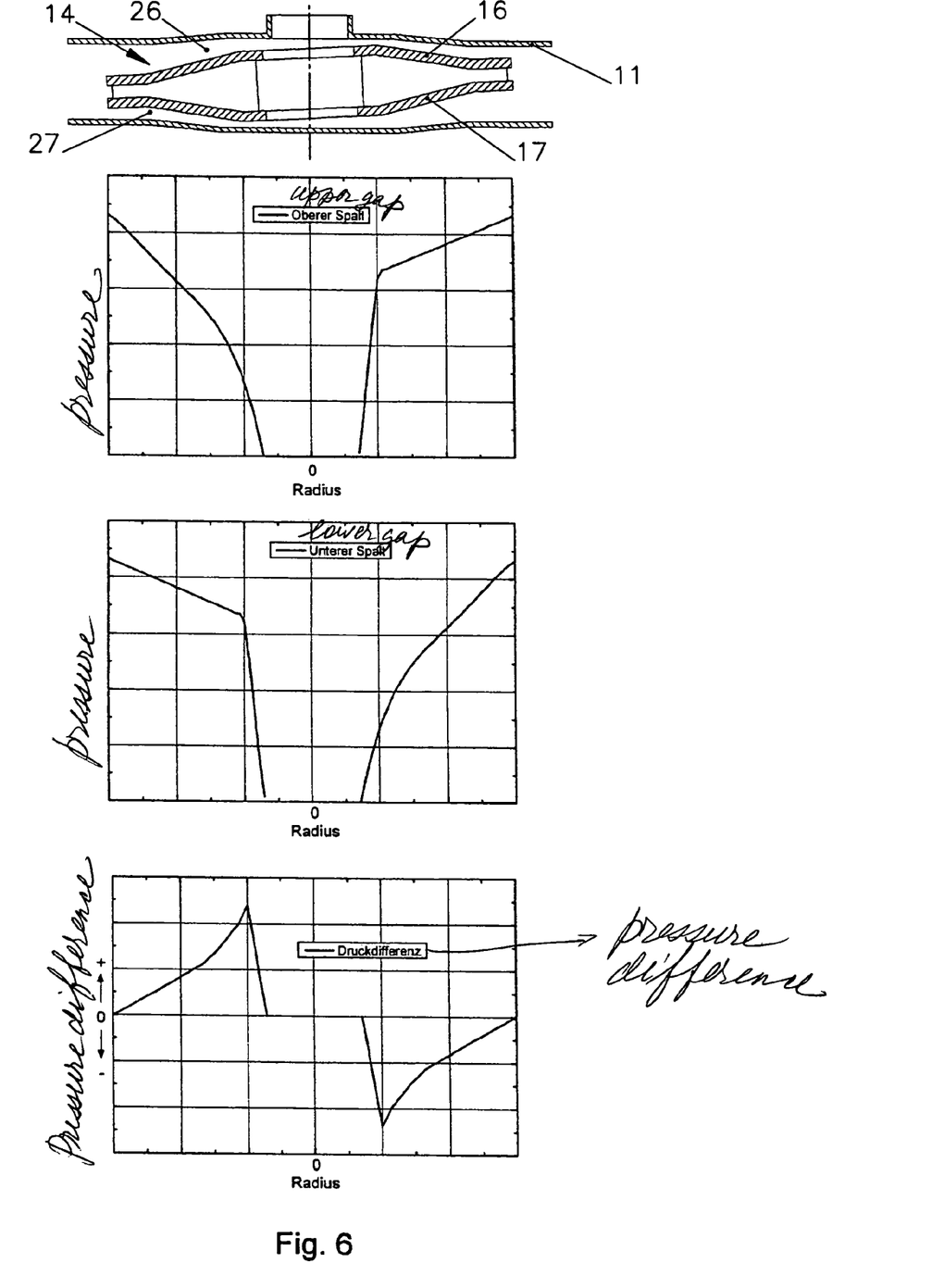
FIG. 6, graphs showing the radial course of the pressures in the rotor side chambers in the event of tilting of the rotor in the housing.

Given a typical geometry of the throttle gap of (h/R)=0.01 and a radial location of the inlet into the throttle gap of $(r_2/R)=0.35$, a rotor of R=20 mm can tilt by an angle of 1.6°, when the throttle gap is radially closed and the rotor runs up at a tangent and at a point at the radius $r_2$. The gap width H at the rotor circumference, in the preferred version, has been found favorable in the range of H/R=0.05±0.01 (H=0.8–1.2 mm). The selected geometry precludes the rotor's striking the wall in the ranges of higher circumferential speeds at the radius R, so that the inflow of the stabilizing back flow into the rotor side chamber is not hindered.

The design of the rotor side chambers and of the throttle gaps in accordance with the invention thus brings about a spatial stabilization of the rotor into its geometrically neutral, symmetrical position in the housing counter to translation in the direction ±z and rotation about the axes x and y.

Figure 7A:
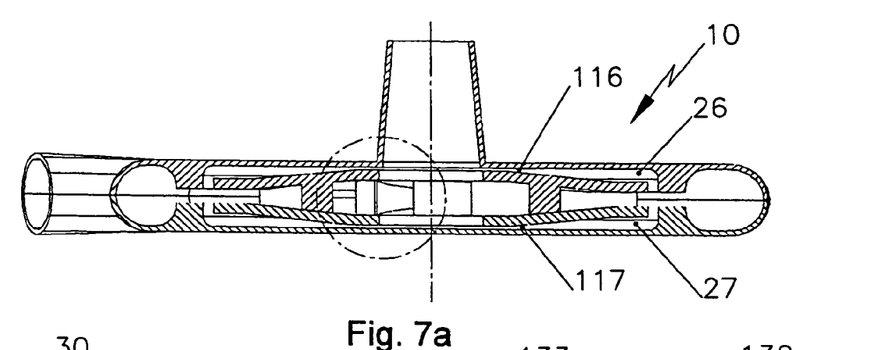
FIGS. 7a, b, c, cross sections through various embodiments of the throttle gap in centrifugal pumps of the invention.
Figure 7B:
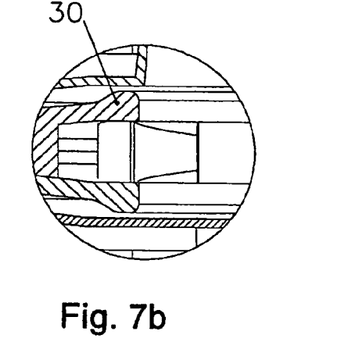
Figure 7C:
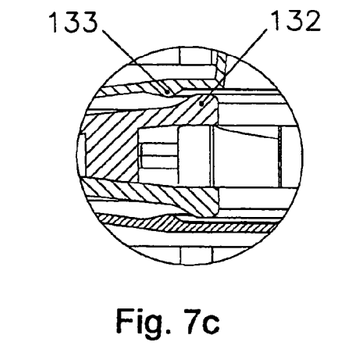

Further possible versions of throttle gaps in pumps according to the invention are shown in FIG. 7. In the pump of FIG. 1, the rotor side chambers 26, 27 taper steadily from the radius R to the inlet into the throttle gap 116, 117 at the radius $r_2$; until the inlet into the rotor at the radius $r_1$, the gap has a constant h, as FIG. 7a shows. In FIG. 7b, one possible variant is shown in which the throttle gap, while preserving the ratios h/R (see above), is formed by a bead 30, which is shaped from the coverings 16, 17 in the region of the radii $r_2$ to $r_1$. In this way, the predominant portion of the rotor side chambers is kept wider, so that the viscous friction there between the rotating rotor and the stationary housing is reduced, and the stabilizing action of the gap is still preserved. In FIG. 7c, a possible variant is shown in which the shape of the coverings with the embodied bead 132 corresponds to FIG. 7b. Here in addition, a bead 133 located radially farther outward is shaped from the housing, and the gap height continues to maintain the ratios h/R according to the invention. In this version, besides the axially stabilizing action of the throttle, a radial force component is generated, which reinforces the centering of the rotor.

The restoring pressure forces become operative very quickly in the event of any positional deviation and hence change in the flow geometry whatever, namely with the propagation speed of the pressure change brought about in the incompressible fluid, or in other words the speed of sound. In blood (as in water), this speed is approximately 1500 m/s (in air, it is approximately 300 m/s). For the geometry shown for the preferred version, a delay in the effectiveness of a positional deviation of the rotor of approximately 50 microseconds is thus calculated.

Unsteady-state numerical simulation calculations, taking forces of acceleration and inertia into account, have shown that sudden changes in position of the rotor are completely compensated for within one to two revolutions. Upon a sinusoidal axial relative motion of the rotor with respect to the housing, a phase displacement between deflection and restoration of approximately 10 ms results, corresponding to approximately one-half a rotor revolution.

This kind of fast response by the position regulation is especially advantageous upon startup of the pump. When the pump is stopped, the rotor is in an incidental, axially displaced or tilted position in the rotor. The stabilizing pressure forces are not generated until during operation. A hydrodynamic suspension of the rotor within its first few revolutions prevents structural damage from friction to the rotor and housing.

The speed and rigidity of the position regulation, according to the invention, of the rotor is also advantageous whenever the person who has an implanted blood pump is exposed in everyday life to varying accelerations in different axes in space. The demonstrated compensation times of approximately 10 ms (100 Hz) with the rigidity of approximately 20 N/mm allow the expectation that the pump rotor will be reliably prevented from striking the housing even upon multiple ground acceleration.

Radial migration of the rotor, that is, translation in the direction ±x and ±y, is not hindered by the above-described axial positional stabilization by pressure forces on the covering. The radial stabilization of the rotor is done passively by reluctance forces. It is advantageous in this respect to keep the destabilizing radial shear, which occurs in every centrifugal pump, slight and to compensate for it. This is successfully done by several provisions:

The radial shear increases in proportion to the total height ($h_2$+2d) of the rotor at the circumference. The rotor is therefore kept especially low in height, and ratios of ($h_2$/R) in the range of from 0.08 to 0.12 and of (d/R) in the range of from 0.05 to 0.1 have proved favorable. An especially low-height design is made possible by the production, according to the invention, of the coverings from solid, biocompatibly coated magnetic material, as a result of which an encapsulation of discrete magnets can be dispensed with.

The radial shear (SR) increases exponentially, if the rotor is not operating at the best point ($Q_{opt}$) of its efficiency: $SR \sim 1-(Q/Q_{opt})^2$ (Bohl, W., Strömungsmaschinen 2, 8th Ed., Vogel Fachbuchverlag, Würzburg (2002)). From FIG. 9 it can be seen that the optimal efficiencies, at the expected rotary speeds of 2400 to 3000 $min^{-1}$, of 5±2 l/min in the operating field of the pump are attained, as a result of which the radial shear is minimized further.

Carrying the volumetric flow away through a spiral conduit with a tangential outlet leads to radial shear whenever a sudden pressure change occurs in the working range in the region of the tongue (cutting edge). According to the invention, this is largely prevented by providing that the volume pumped by the rotor, before entering the spiral conduit, passes through a circular annular gap, whereupon a rectification of the flow ensues. The further outflow of the fluid accordingly takes place via the spiral conduit, which can be embodied as an Archimedes spiral of approximately circular cross section. An axial height $h_3$ of the annular gap of $h_3/h_2$ in the range of from 0.6 to 2.0, a radial length $(r_4/r_5)$ in the range of from 0.8 to 1.0, and a circular cross section, increasing steadily over the circumference of the spiral conduit, with a diameter $h_3$ at the tongue and a terminal diameter at the tangential outflow of $4 \cdot h_3$ have proved favorable in the context of the invention. With this preferred geometry, in the range of maximum efficiency, no radially destabilizing sudden pressure change occurs in the region of the tongue.

The three characteristics described for reducing radial shear can largely minimize it but not compensate for it. For that purpose, the aforementioned magnetic reluctance forces generated by the stator and rotor geometries are used.

The hydraulic efficiency of an implantable blood pump should be as high as possible, since any power loss caused by viscous friction, turbulence, and short-circuit flows contributes to blood damage and is finally transmitted to the blood as thermal energy. A further factor is that the power demands made of the electric drive mechanism and the energy expenditure required for that purpose decrease inversely proportionally, which is favorable to the miniaturization desired.

Figure 8:
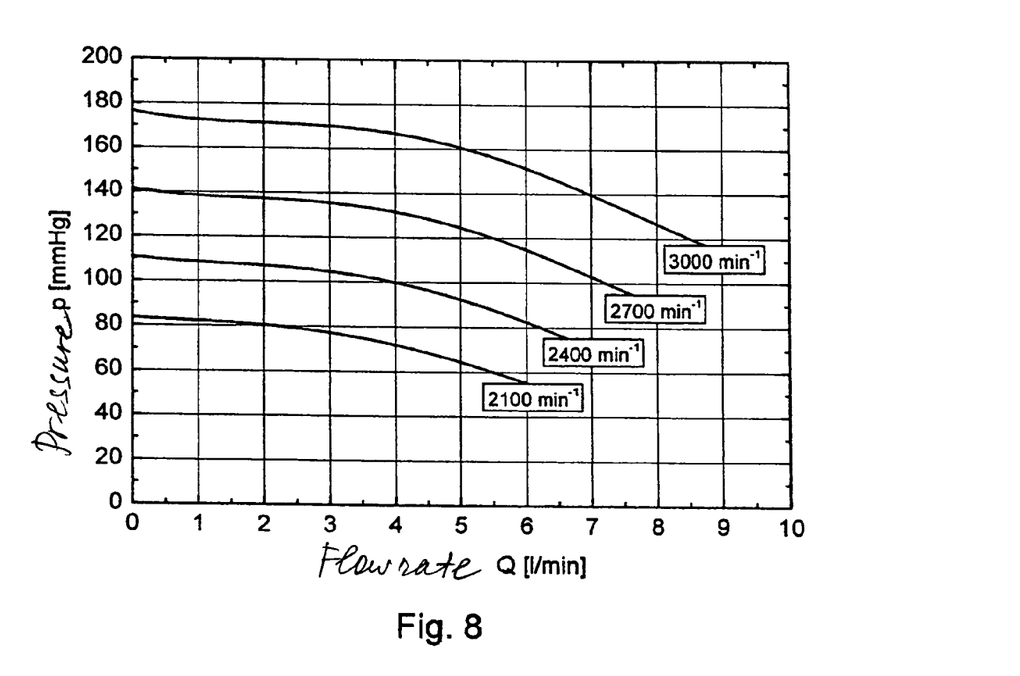
FIG. 8, throttle curves of the pump of the invention for different rotary speeds.

By means of the described geometry of the wheel side chambers and the conduits leading away, and in combination with a covered rotor with optimal blading, previously unknown efficiencies are attained. This is demonstrated in FIG. 8 and FIG. 9 in terms of measured throttle curves and associated efficiencies. In the typical operating range of the pump of the pump of 5±2 l/min flow rate, at pressures of 120±20 mmHg, the hydraulic pump powers (p·V) amount to 1.4±0.7 watts. The rotary speeds required for this are in the range from 2400 to 3000 $\text{min}^{-1}$.

Figure 9:
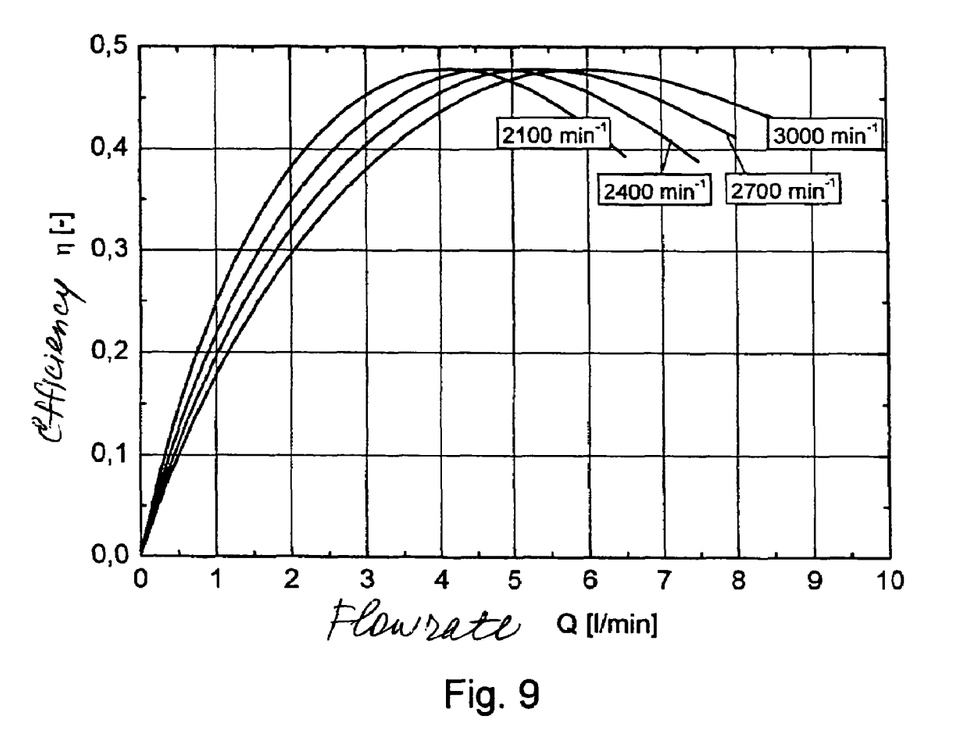
FIG. 9, graphs showing the hydraulic efficiencies over the flow rate of the pump of FIG. 1 at different rotary speeds.

When a test fluid with the viscosity of blood (4 mPas) is used, the pump of FIG. 1 has the efficiencies shown in FIG. 9, which in the typical operating range amount to from 0.4 to 0.47. This is approximately equivalent to four times the values that have been given for known blood pumps.

The required shaft power of approximately 3±1.5 watts is correspondingly low, which is an especially favorable prerequisite for miniaturizing the drive and the power supply.

For the hydrodynamic stabilization according to the invention of the rotor, the efficiency-reducing back flows in the rotor side chamber are utilized. In the typical operating range these amount to approximately 2 to 3 l/min. To generate a net flow rate of 5 l/min, accordingly from 7 to 8 l/min must be demanded of the rotor. This is equivalent to a hydraulic additional power of 0.5 to 0.8 watts for stabilizing the rotor, and thus an additional need of only approximately 20% in terms of shaft power. However, that need not be additionally exerted, but instead originates in the wasted/dissipated energy of the leakage flows that has gone unused in other pumps.

The pump according to the invention is especially effective and is intended to pump the blood in as protective a way as possible. The most important prerequisite for this is the avoidance of high shear stresses. The blood pump is distinguished from known pumps with hydrodynamic slide bearings and others in that the gap spaces between the rotor and the pump housing are kept wide. Even in the small region of the throttle gaps that rotate slowly near the axis, the gap heights, in comparison to known pumps with hydrodynamic bearing by wedge faces, amount to a multiple of the values given for the known pumps, and the shear stresses that occur are correspondingly slight.

At the maximum rotary speed of the rotor to be expected in operation, which is 3000 $\text{min}^{-1}$, the circumferential speed in the throttle gap is only $\gamma = 1.8$ m/s, and for a gap height h of 0.2 mm, a shear degree $ã = \gamma/h$ of 9000 $\text{s}^{-1}$ is calculated. With the typical viscosity ($\eta$) of the blood of 4 mPas, the resultant mean shear stress is $\tau = \gamma \cdot \eta$ of 36 $\text{Nm}^{-2}$. This is accordingly one order of magnitude below the limit value of 400 $\text{Nm}^{-2}$, which according to recent studies is considered critical for blood damage from shear forces (Paul, R., et al, *Shear stress related blooddamage in laminar couette flow*. Artif Organs, 2003. 27(6): p. 517-29).

The cumulative traumatization (BT) of a blood volume (V) upon passage through a zone of high shear stress $\tau$ also correlates with the exposure time (t) in accordance with the relation BT~(V·$\tau$·t). Numerical simulation calculations have shown that the mean passage time of the blood through the entire pump, at a flow rate of 5 l/min, is approximately 100 ms, and a particle remains in the throttle gap for at most approximately 0.3 ms in a shear field of below 40 N/m². The instantaneous blood volume in the throttle gaps is only 15 mm³. Such favorable flow-dynamic prerequisites for low blood damage have not been reported before.

Along with the mechanical cell destruction from shear stresses and wall contacts, the activation of the cellular and molecular mechanisms of blood coagulation is a central problem in implantable blood pumps. Clots that block pumps or are carried away as emboli and can cause such complications as strokes and renal infarctions occur preferentially as a result of contact activation at foreign surfaces and also in flow stasis zones and standing eddies. The blood of the invention has no such flow regions; instead, all the chambers that carry blood are constantly purged with a high flow speed and a short dwell time. The surface of all the stationary and rotating components is smooth, and steps and profile sections in the flow direction are avoided. All the preferred versions can be made from biocompatible materials and provided with an anticoagulant coating, such as surface-bonded heparin.

From the mechanisms of the invention, described thus far, for hydrodynamic suspension of the pump rotor, it finally follows that the rotor is positioned centrally in the housing in the axial direction by the effects of the throttle gap. In the radial direction, it requires the additional support of magnetic reluctance forces. In operation, the rotor will dynamically shift, tumble, and run eccentrically. Because of the sufficient spacing from the walls and the fast reaction time of the stabilizing forces, however, it will not hit the wall at any time. The desired mobility of the rotor in the housing is expressly wanted, since only in this inventive combination of the aforementioned characteristics can safe operation, high efficiency, constant purging of all the blood-carrying chambers, and the least blood damage be achieved.

The contactless drive of the pump rotor can be done, in a preferred version, in the form of a permanent-magnetically excited, two-strand electrical disk rotor synchronous machine.

The hydrodynamic suspension of the rotor of the pump dictates a disadvantageously large magnetic air gap between the stator heads for the electrical drive mechanism. This is necessary for receiving all the housing walls, the blood-carrying rotor side chambers, and the rotor itself. The air gap must amount to $L = 0.1$ to $0.15 \cdot R$, and thus in motor construction makes unusual demands in terms of optimizing the electromechanical efficiency of the drive mechanism.

One criterion that must be met is, with minimum mass of the permanent magnets and hence little axial magnetic rigidity, to generate maximum torque at high electromechanical efficiency, while avoiding resting moments and waviness of the torque.

In the pump of the invention, this problem is solved as follows: The permanent magnets are divided, by the accommodation in the two rotor coverings, and two planes, between which a magnetic short circuit exists via the blade conduit. In a preferred version of the rotor with R=20 mm, d=1 mm and $r_3$=16 mm, only 5 g of magnet mass (NdFeB) is then needed, with correspondingly little destabilization of the rotor upon axial deflection.

According to the invention, the two stators can be rotated counter to one another by an amount of from ⅓ to ½ the pole spacing, or in other words, for 6 poles, by 20 to 30 degrees. The permanent magnet regions of the two rotor coverings can also be rotated counter to one another by up to ⅙ the pole spacing, or in other words by up to 10 degrees. Both provisions contribute to suppressing resting moments and waviness of the torque.

A further increase in the electromechanical efficiency, with minimal axial rigidity of the drive mechanism, can be accomplished by optimized pole coverage and of the relative pole coverage of the permanent magnets.

The radial stabilization of the rotor position (translation in the x and y directions) is promoted, but not effected, by the above-described design of the rotor, the rotor side chambers, the circular annular gap, and the spiral conduit that carries the flow away. The radial centering of the rotor is effected by means of magnetic reluctance forces between the permanent magnet regions in the rotor and the head regions of the stator teeth. In pump operation, the stabilizing is further reinforced by the gyroscopic forces acting on the rotor.

The invention claimed is:

1. A centrifugal pump, comprising a housing which is closed in a fluid-and gas-tight fashion except for at least one inlet opening and at least one outlet opening; a pump rotor located inside said housing rotatably and being simultaneously a rotor of a drive motor, said rotor being hollow and having an inlet at an intake side for entering a fluid into the rotor and an outlet for leaving the fluid from the rotor so that the fluid flows through the rotor, said rotor having at least one permanently magnetized region; one stator located outside said housing, above and below said rotor, so that said stators in a gap between said stators and said permanently magnetized region of said rotor, generate a magnetic flux, said rotor being arranged symmetrically to its central plane and having an upper and a lower covering, an element selected from the group consisting of said rotor, said housing and both being shaped such that axial spaces between said upper and lower coverings and an upper and a lower housing wall decrease continuously radially inwards, in such a manner that in a radially inner region of said rotor, rotor side chambers each have one throttle gap which in operation affect a radially inwards-oriented backflows in said rotor side chambers such that upon an axial deflection of said rotor, different pressure distributions occur above and below said rotor, as a result of which forces acting on a predominant surface area of said coverings are generated which effect an axial stabilization of said rotor and are operative in a same way against tilting of said rotor in said housing; and said rotor having blades being disposed between said upper and lower coverings inside the rotor, outer surfaces of said upper and lower coverings being smooth.

2. A centrifugal pump as defined in claim 1, wherein said rotor of said drive motor has a plurality of magnetized regions distributed uniformly over its circumference.

3. A centrifugal pump as defined in claim 1, wherein said rotor is arranged so that a radial centering of said rotor is effected passively by reluctance forces.

4. A centrifugal pump as defined in claim 1, wherein said rotor is composed entirely of a material selected from the group consisting of a paramagnetic material, a ferromagnetic material, and both.

5. A centrifugal pump as defined in claim 1, wherein parts of the centrifugal pump are configured so that at least their surfaces that are in fluid contact are provided with a coating adapted to properties of a fluid.

6. A centrifugal pump as defined in claim 1, wherein the centrifugal pump is configured as a blood pump that is implantable in a body.

7. A centrifugal pump as defined in claim 1, wherein said centrifugal pump is configured as a pump for blood in cardiac substitution or assist devices.

* * * * *